United States Patent [19]
Jensen

[11] Patent Number: 5,255,024
[45] Date of Patent: Oct. 19, 1993

[54] EYE DROP ALIGNMENT GLASSES

[76] Inventor: Charles W. Jensen, Rte. 4 Box 30-41, Lake Geneva, Wis. 53147

[21] Appl. No.: 20,425

[22] Filed: Feb. 22, 1993

[51] Int. Cl.[5] .......................... G02C 1/00; A61M 35/00
[52] U.S. Cl. ...................................... 351/158; 351/41; 604/300
[58] Field of Search .................. 351/41, 158; 604/300, 604/301, 302

[56] References Cited

U.S. PATENT DOCUMENTS

| | | | |
|---|---|---|---|
| 2,316,817 | 4/1943 | Splaine | 351/137 |
| 3,446,209 | 5/1969 | Macha | 351/158 |
| 4,183,355 | 1/1980 | Meckler | 604/302 |
| 4,468,103 | 8/1984 | Meckler | 351/158 |

FOREIGN PATENT DOCUMENTS

| | | | |
|---|---|---|---|
| 2362147 | 6/1975 | Fed. Rep. of Germany | 604/302 |
| 3634603 | 9/1987 | Fed. Rep. of Germany | 604/302 |
| 2635011 | 2/1990 | France | 604/300 |

Primary Examiner—Martin Lerner
Assistant Examiner—R. D. Shafer
Attorney, Agent, or Firm—Kajane McManus

[57] ABSTRACT

The eyedrop alignment glasses have a slot in the lenses thereof. Over each slot is provided a pivotable slide member having a bore therein which aligns with the slot. The tip of a dropper is engaged within the bore, with the slide being movable to center the tip over the user's eyeball. Further, the glasses are adjustable in distance from the user's eyeball to accommodate dropper tips of varying length.

3 Claims, 1 Drawing Sheet

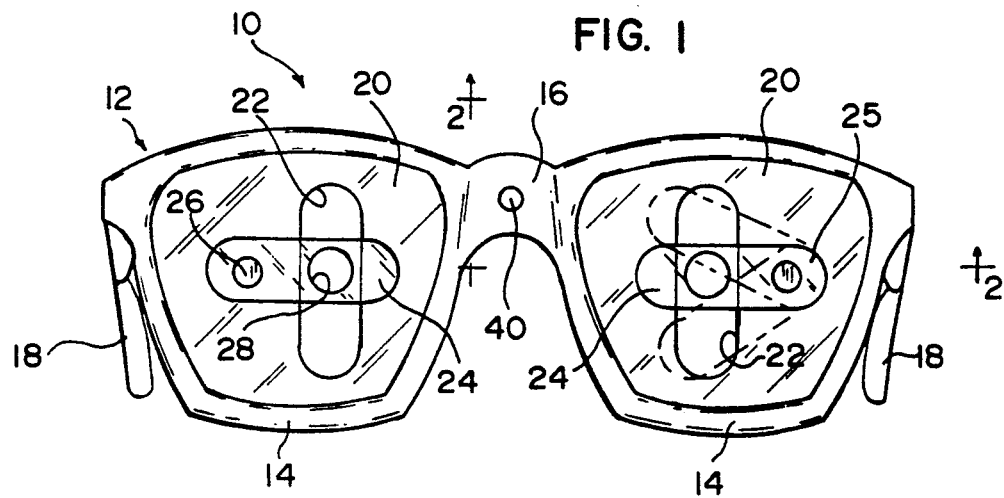
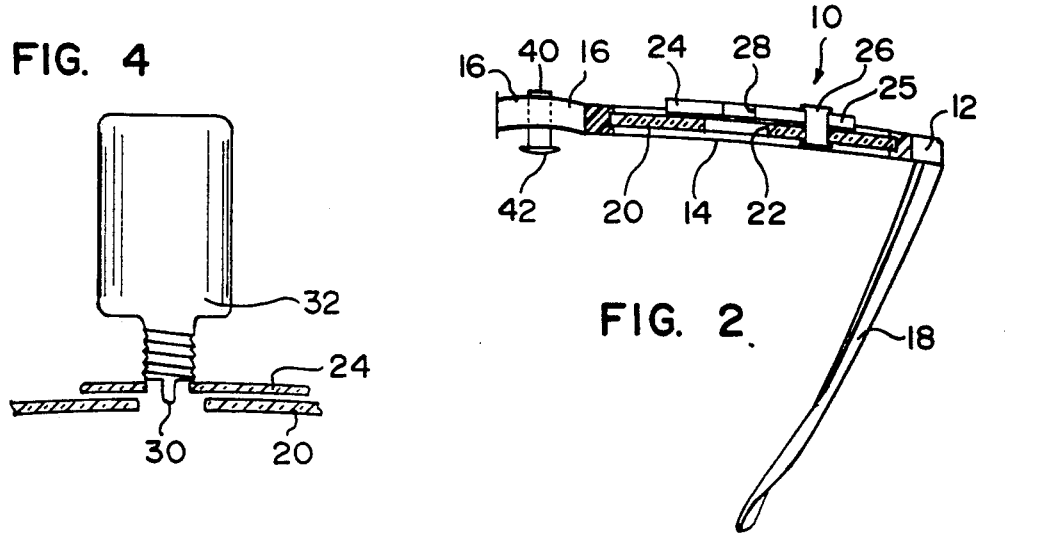
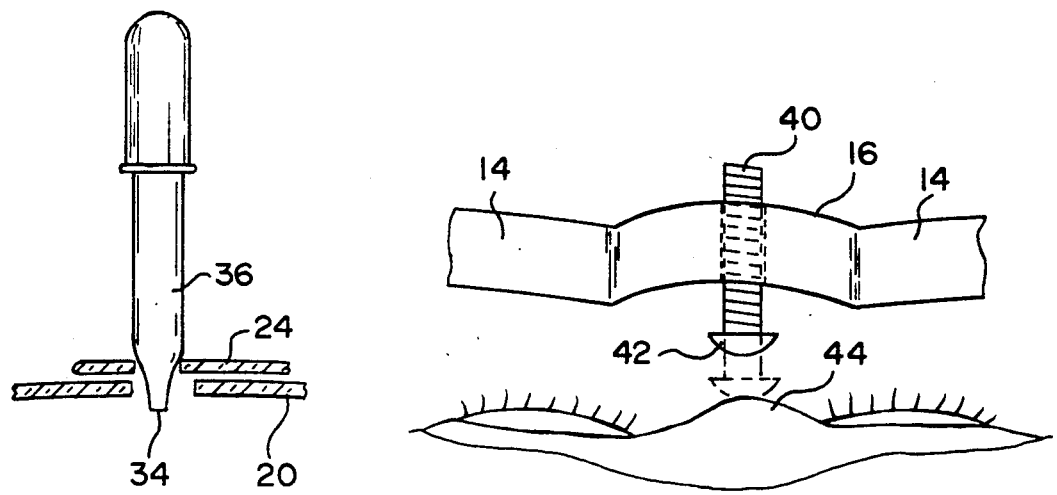

EYE DROP ALIGNMENT GLASSES

BACKGROUND OF THE INVENTION

1. Field of the Invention

The present invention relates to a pair of glasses which include a moveable element and an opening in each of the lenses thereof to accommodate alignment of a tip of an eye drop dispensing structure relative to the eyes of the user. More particularly, the glasses include structure for engaging the drop dispensing structure in a near centered position over the eyeballs of the user and further include structure for allowing a tip of the dispensing structure to be moved toward or away from the eyeball, as necessary.

2. Description of the Prior Art

Heretofore various alignment devices for assisting a user in self application of eye drops have been proposed.

Such devices are disclosed in the Macha U.S. Pat. No. 3,446,209 and the Meckler U.S. Pat. No. 4,183,355.

Both of these patents disclose eye drop alignment devices in the form of glasses having alignable openings therein for receiving the end of a medication dropper therein.

However, it will be understood that the length of the tip of the medication droppers differs from dropper to dropper. Therefore, at times it becomes necessary to be able to move the openings toward, or more importantly, away from, the user's eyes to keep from contacting or injuring the eyeball or lids with the tip of the dropper.

As will be described in greater detail hereinafter, the eye drop alignment glasses of the present invention not only align the dropper to center same over each eyeball but also allows for adjustment relative to length of the dropper tip.

SUMMARY OF THE INVENTION

According to the invention there are provided eyedrop alignment glasses comprising a frame including two lens rims joined together by a bridge. The frame also has a pair of temples extending rearwardly therefrom. A lens having an elongated slot therein is engaged within each lens rim, the slots being off center in the lenses and closer to the bridge. A pivotable slide member having a bore therein extends across the slot in a manner to maintain the bore overlying the slot. Structure is provided on the frame bridge which is adjustable to raise and lower the frames relative to the eyes of a user.

BRIEF DESCRIPTION OF THE DRAWINGS

FIG. 1 is a top plan view of the eye drop alignment glasses of the present invention.

FIG. 2 is a cross sectional view through the glasses and is taken along line 2—2 of FIG. 1.

FIG. 3 is an enlarged view of the bridge of the glasses showing a spacer element thereof for use in moving the glasses toward or away from the user's eyes.

FIG. 4 is a perspective view showing a tip of a bottle of eyedrops engaged within an opening for same in one of the lenses.

FIG. 5 is a perspective view showing an eye dropper being used in place of a dropper bottle.

DESCRIPTION OF THE PREFERRED EMBODIMENT

Referring now to the drawings in greater detail therein, there is shown therein the eye drop alignment glasses made in accordance with the teachings of the present invention and generally identified by the reference numeral 10.

As shown, the glasses include a frame 12 having a pair of lens rims 14 joined together by a bridge 16. Each lens rim 14 engages a temple 18 extending rearwardly therefrom.

Within each lens rim 14 is a lens 20 within which an elongate slot 22 has been formed, the slot 22 extending vertically in FIG. 1 and being positioned off center, toward the bridge 16.

Positioned across each lens 20 in a direction substantially transverse to the slot 22, is a pivotable slide member 24, one end 25 of which is fixed to the lens 20 by a stud or like structure 26 in a manner to be pivotable thereabout. The slide member 24 has a bore 28 therein which is substantially centered over the slot 22 when the slide member 24 is placed perpendicular to the slot 22.

Throughout the course of pivoting of the slide member 24 about the stud 26, the bore 28 remains interposed over a portion of the slot 22.

Such pivotable slide member 24 is provided because it is desired to center the drops to be administered and, not every user has an identical eyeball placement in the vertical direction of FIG. 1. By looking into a mirror with the glasses 10 on, the slide members 24 can be positioned to center the drops over the eyeball.

A further accommodation may at times be required. Such accommodation is in a direction toward and away from the user's eyeball. In this respect, not every device used for administering eye drops has an identical length tip. For example, the tip 30 of a dropper bottle 32 may be of a different length than the tip 34 of a dropper 36. To keep a user from having the tip 30, 34 engage directly against the eyeball, it is desirable to have a degree of adjustability in moving the frame 12 toward or away from the user's eyes.

Such adjustability is provided in the glasses 10 of the present invention by providing an adjustment member in the form of a screw 40 on the bridge 16. This screw 40 can be threadedly extended or retracted to position the tip 30, 34 appropriately relative to the eyeball of the user, the head 42 of the screw 40 resting against the bridge 44 of the user's nose to position the frames 12 at a desired height relative to the eyes.

As described above, the glasses 10 of the present invention provide advantage over the art, some of which have been described above and others of which are inherent in the invention. Also, modifications can be proposed to the glasses 10 without departing from the teachings herein. Accordingly, the scope of the invention is only to be limited as necessitated by the accompanying claims.

I claim:

1. Eyedrop alignment glasses comprising;
   a frame including two lens rims joined together by a bride, said frame also having a pair of temples extending rearwardly therefrom;
   a leg engaged in each lens rim and having an elongated slot engaged in each lens and therein the slot being off center in the lens and close to the bridge;

a slide member extending across the lens and being pivotably fixed at one end thereof to the lens by a stud, the slide member having a bore therein and extending across the slot in a manner to maintain the bore overlying the slot; and an adjustment member on the bridge which is adjustable to raise and lower the frame relative to the eyes of the user.

2. The glasses of claim 1 wherein said adjustable member on said bridge comprise a screw.

3. The glasses of claim 2 wherein said screw has a head, the head extending in the same direction as the temples.

* * * * *